United States Patent [19]

Singaram et al.

[11] Patent Number: 5,367,073
[45] Date of Patent: Nov. 22, 1994

[54] ASYMMETRIC SYNTHESIS OF β-AMINO ALCOHOLS FROM CHIRAL OR ACHIRAL ENAMINES

[75] Inventors: Bakthan Singaram, Santa Cruz; Gary B. Fisher, Boulder Creek, both of Calif.; Christian T. Goralski; Lawrence W. Nicholson, both of Midland, Mich.

[73] Assignee: The Regents of the University of California, Oakland, Calif.

[21] Appl. No.: 138,613

[22] Filed: Oct. 15, 1993

Related U.S. Application Data

[63] Continuation of Ser. No. 847,171, Mar. 6, 1992, abandoned, which is a continuation-in-part of Ser. No. 848,427, Mar. 6, 1992, abandoned.

[51] Int. Cl.$^5$ ............... C07C 213/00; C07C 215/08; C07C 213/38; C07D 207/12; C07D 295/08
[52] U.S. Cl. .................... 544/170; 546/344; 548/570; 564/382; 564/383; 564/404; 564/424; 564/503; 568/1; 568/7
[58] Field of Search ............... 564/382, 383; 544/170; 546/344; 548/570

[56] References Cited

U.S. PATENT DOCUMENTS

| 4,476,324 | 10/1984 | Reichle | 568/338 |
|---|---|---|---|
| 4,886,924 | 12/1989 | Goralski | 358/318 |
| 4,895,996 | 1/1990 | Goralski | 565/328 |
| 5,194,613 | 3/1993 | King | 544/352 |

FOREIGN PATENT DOCUMENTS

| 0158319 | 10/1985 | European Pat. Off. | 544/352 |
|---|---|---|---|
| 0263463 | 4/1988 | European Pat. Off. | 544/352 |
| 0310689 | 4/1989 | European Pat. Off. | 487/241 |
| 0318099 | 5/1989 | European Pat. Off. | 487/241 |
| 350910 | 1/1990 | European Pat. Off. | 544/352 |
| 2434913 | 2/1975 | Germany | 487/241 |
| 85563 | 11/1984 | Romania | 544/352 |
| 8703592 | 6/1987 | WIPO | 544/352 |
| 8905810 | 6/1989 | WIPO | 487/241 |

OTHER PUBLICATIONS

Borowitz et al, J. Org. Chem., vol. 32, pp. 4157–4160 (1967).
Goralski et al, J. Org. Chem., vol. 52, pp. 4014–4019 (1987).
Mueller et al, Tetrahedron Letters, vol. 21, pp. 1093–1098 (1980).
H. C. Brown et al., Accounts of Chem. Research, vol. 21, No. 8, Aug. 1988, p. 287. "Development of a Simple General Procedure for Synthesis of Pure Enantiomers via Chiral Organobanes".
B. Singaram et al., J. Org. Chem., 1991, vol. 56, p. 1543. "Hydroboration. 86. Convenient Conversion of Aldehydes and Ketones into the Corresponding Alkenes via Hydroboration of the Enamines."
B. Singaram et al., J. of Org. Chem., 1991, vol. 56, p. 5691. "Unusual Directive Effects in the Hydroboration of beta, beta-Disubstituted Enamines. Conversion of alpha-Substituted Aldehydes to the Corresponding Alkenes and beta-Amino Alcohols."
A. Hajos, Complex Hydrides, 1979, Pub.: Elsevier, New York, N.Y. Common reference book; title page and Table of Contents included.
H. C. Brown, et al., 1956, Journal of the American Chemical Society, vol. 78, p. 3616. "The Preparation of Sodium Triisopropoxyborohydride and Tri-t-butoxyborohydride. The Effect of Alkoxy Substituents on the Reducing Properties of Borohydride Ion."
H. C. Brown, et al., 1953, Journal of the American Chemical Society, vol. 75, p. 6263. "Addition Compounds of Alkali Metal Hydrides. II. Sodium Trimethoxyborohydride as a Reducing Agent for Organic Compounds".
C. A. Brown, et al., 1973, Journal of the Chemical Society, Chemical Communications, 1973, p. 391. "Potassium Tri-isopropoxyborohydride. A New Mild Complex Hydride Reducing Agent with High Stereoselectivity for Reduction of Ketone".
J. H. Golden, et al., 1992, Inorganic Chemistry, vol. 31, p. 1533. "Disproportion of Alkoxyborohydrides: A $^{11}$B NMR Study of the Reaction between Sodium Borohydride and Fluorinated Alcohols and Phenols. The Preparation of Tris(fluoroalkoxy)- and Tris(fluorophenoxy)borohydrides".

(List continued on next page.)

Primary Examiner—Floyd D. Higel
Attorney, Agent, or Firm—Phillips Moore Lempio & Finley

[57] ABSTRACT

The present invention relates to a process for the synthesis of chiral enantiomerically pure β-amino alcohols which are extraordinarily important as therapeutic agents for the treatment of a variety of human disorders and as chiral auxiliaries in organic synthesis. The hydroboration of enamines is a versatile and convenient method for the synthesis of both racemic and enantiomerically pure β-amino alcohols in high yields. This methodology enables the synthesis of virtually any β-amino alcohol. Hydroboration of these enamines with chiral organic borohydrides, e.g. either mono- or diisopinocampheylborane, followed by oxidation with aqueous or solid NaOH/30% $H_2O_2$ or $Me_3NO$, gives the corresponding chiral β-amino alcohol. Enantiomeric excesses ranged from 60% for reactions run at 25° C. to greater than 99% for reactions run at −25° C.

17 Claims, 1 Drawing Sheet

OTHER PUBLICATIONS

H. C. Brown, et al., *Journal of Organic Chemistry*, vol. 49, p. 885. "Selective Reductions. 33. Potassium Triisopropoxyborohydride as a Selective Reducing Agent in Organic Synthesis. reaction with Selected Organic Compoyunds Containing Representative Functional Groups".

E. R. Garret et al., 1953, *Journal of American Chemical Society*, vol. 75, p. 6051. "The Kinetics of 20-Keto reduction in 11α-Acetoxypregnane-3,20-dione by Sodium Borohydride".

H. Haubenstock et al., 1962, *Journal of American Chemical Society*, vol. 84, p. 2368. "Reductions with Metal Hydrides. XI. Solvent Effect on the Stereochemistry of Reduction with Sodium Borohydride".

A. L. Allred et al., 1958, *Journal of Inorganic Nuclear Chemistry*, vol. 5, p. 264. "A Scale of Electronegativity Based on Electrostatic Force".

F. A. Davis et al., 1971, *Journal of Organic Chemistry*, vol. 36, p. 1300. "The Effect of Alkyl Substitution on the Boron-11 Chemical Shifts in Aminoboranes and Borates".

R. O. Hutchins et al., 1984, *Journal of Organic Chemistry*, vol. 49, p. 2438. "Aminoborohydrides as Reducing Agents. 1. Sodium (Dimethylamino)- and (tert-Butylamino)borohydriedes as Selective Reducing Agents".

H. C. Brown et al., 1982, *Organometallic Chemistry*, vol. 239, p. 43. "Investigations in the Synthesis of Alkyl-substituted Borohydrides".

E. R. H. Walker, *Chemical Society Review*, 1976, vol. 5, p. 23. "The Functional Group Selectivity of Complex Hydride Reducing Agents".

March, J., Advanced Organic Chemistry: Reactions, Mechanisms and Structure, 1968, pp. 435-436.

Tundo, Pietro et al., Ind. Eng. Chem. Res., 1988, 27, pp. 1565-1571.

Bianche, P., Chemical Abstracts: 1-Pharmacology, Sep. 15, 1986, pp. 1-2.

ASYMMETRIC SYNTHESIS OF β-AMINO ALCOHOLS FROM CHIRAL OR ACHIRAL ENAMINES

This is a continuation of copending application of Ser. No. 07/847,171 filed on Mar. 6, 1992, now abandoned, which is a continuation-in-part of the application Ser. No. 07/848,427 filed on Mar. 6, 1992, now abandoned.

BACKGROUND OF THE INVENTION

1. Source of the Invention

This invention was made with support from Dow Chemical Company under Contract No. 443120-57276-3. Dow Chemical Company may have some rights in this invention.

2. Field of the Invention

The present invention concerns the asymmetric synthesis of beta-amino alcohols from chiral or achiral enamines. The synthesis utilizes chiral organoboranes having a high steric bulk under conventional hydroboration conditions.

3. Description of the Related Art

Enantiomerically pure beta-amino alcohols play an increasingly important role in the treatment of a wide variety of human disorders, see Ref. (1) below. These alcohols are also useful as chiral auxiliaries in organic synthesis, see Ref. (2).

A commercially safe, economical route to chiral amino alcohols has been the goal of a number of academic and industrial groups. Some art of general interest is as follows:

C. T. Goralski et al., U.S. Pat. No. 4,886,924.
C. T. Goralski et al., U.S. Pat. No. 4,895,996.
H. C. Brown et al. (1988) *Accounts for Chemical Research*, Vol. 21 (#8), p. 287.

More specific references are described below and are referred to in the subsequent text as (Ref. 1) or (1), etc. Some art of interest is listed as follows:

1. M. Grayson, Ed. (1982), *Kirk-Othmer Encyclopedia of Chemical Techology*, Vol. 17, pp. 311–345.
2. (a) K. Tomioka (1990) *Synthesis*, p. 541; (b) R. Noyori et al., (1991) *Ang. Chem. Int. Ed. Engl.*, Vol. 1, p. 49.
3. (a) S. Miyano et al. (1981) *J. Org. Chem.*, Vol. 48, p. 3608; (b) W. H. Frishman (1981) *New Eng. J. Med.*, Vol. 305, p. 500; (c) R. J. Lefkowitz, *Ann. Rep. Med. Chem.*, Vol. 15, p. 217; (d) E.J. Corey, et al. (1991) *J. Org. Chem.*, Vol. 56, p. 442.
4. (a) D. Enders (1981) ChemTech, Vol. 8, p. 504; (b) G.M. Coppola et al. (1987) *Asymmetric Synthesis: Construction of Chiral Molecules Using Amino Acids*, Wiley-Interscience: New York, p. 1–4.
5. (a) M. Kitamura et al. (1989) *J. Am. Chem. Soc.*, Vol. 111, p. 6071; (b) M. Kitmura (1989) *J. Am. Chem. Soc.*, Vol. 111, p. 4028; (c) N. Oguni et al. (1988) *J. Am. Chem. Soc.*, Vol. 110, p. 7877; (d) K. Soai et al. (1987) *J. Am. Chem. Soc.*, Vol. 109, p. 7111; (e) E. Corey et al. (1986) *J. Am. Chem. Soc.*, Vol. 108, p. 7114; (f) T. Imamoto et al. (1980) *Chem. Lett.* p. 45; (g) F. Leyendecker et al. (1983) *Tetrahedron Lett.*, Vol. 24, p. 3513.
6. J. March (1985) *Advanced Organic Chemistry*, 3rd Ed., Wiley-Interscience: New York, pp. 368, 738–740.
7. (a) G.M. Coppola et al. (1987), *Asymmetric Synthesis: Construction of Chiral Molecules Using Amino Acids,* Wiley Interscience, New York, N.Y., pp. 53, 85, 115, 133, 159, 188.
   (b) L. Overman et al. (1985) *J. Org. Chem.*, Vol. 50, p. 4154.
8. (a) H. Brown et al. (1987) *J. Org. Chem.*, Vol. 52, p. 4014; (b) C. Goralski (1987) *Final Report*, R. B. Wetherill Laboratories of Chemistry, Department of Chemistry, Purdue University; (c) B. Singaram et al. (1991) *J. Org. Chem., Vol.* 56, p. 5691.
9. (a) H. Brown et al. (1989) *J. Am. Chem. Soc.*, Vol. 111, p. 384; (b) B. Singaram et al. (1991) *J. Org. Chem.*, Vol. 56, p. 1543.

All patents, patent applications, articles, standards etc. cited in this application are incorporated herein by reference in their entirety.

Some examples of β-amino alcohols that serve as valuable therapeutic agents are the β-blockers Bevantolol, (Ref. 3a), Denopamine (3d) and Propranolol (3b,c) shown below:

Bevantolol

Denopamine

Propranolol

The importance of enantiomeric purity in pharmaceutical compounds has been demonstrated by the debilitating and sometimes tragic side-effects caused by the presence of the non-therapeutic enantiomer of an otherwise beneficial drug (Ref. 1,3b,4). Naproxen is one isomer of a chiral antiinflammatory drug used extensively for arthritis. Naproxen must be resolved into the (R) and (S) forms. The (S)-isomer is therapeutic. The (R)-isomer concentrates in the human liver and can be fatal. One optical isomer of thalidomide is therapeutic. The other isomer causes severe birth defects (4).

Figure 1:
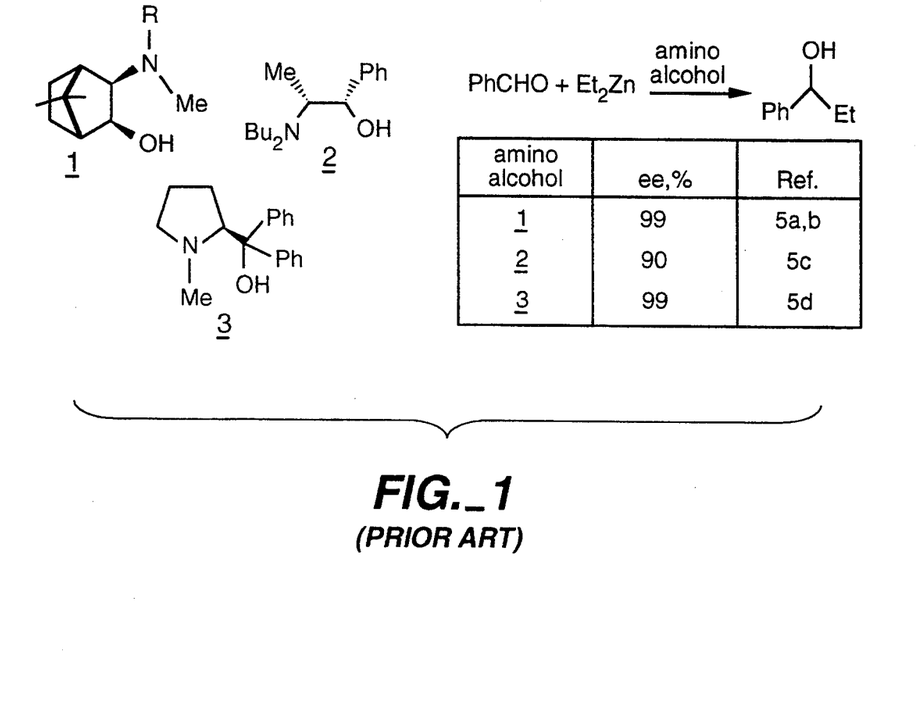
FIG. 1 shows the known process to produce enantiomerically pure amino alcohols as chiral auxiliaries in diethylzinc additions to benzaldehyde.
Figure 2:
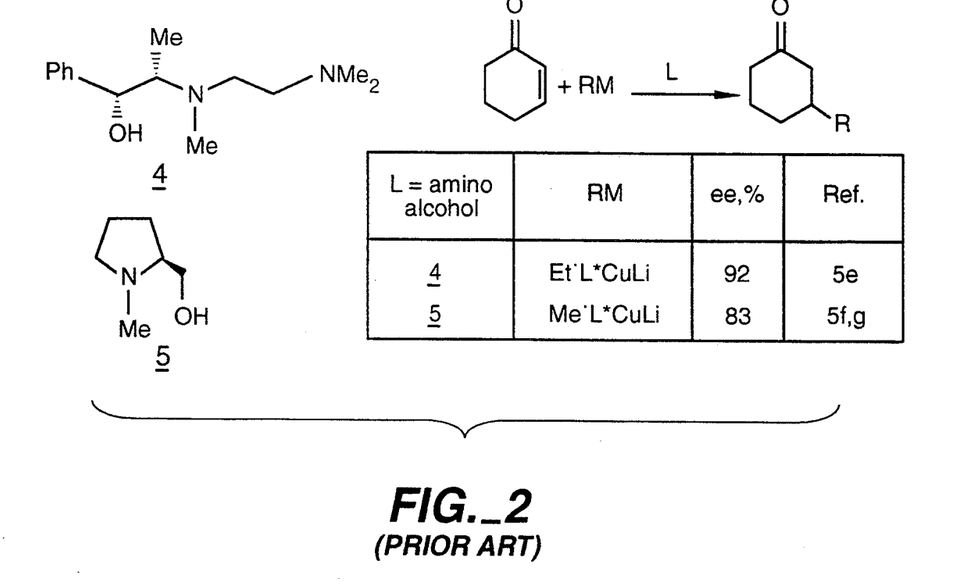
FIG. 2 shows the known process to produce enantiomerically pure amino alcohols as chiral auxiliaries in organocuprate additions to cyclohexenone.

Enantiomerically pure β-amino alcohols have also been shown to be exceedingly effective chiral auxiliaries in asymmetric carbon-carbon bond forming reactions such as additions of diethylzinc to aldehydes (5a,5d) (see FIG. 1), or conjugate additions of organocuprate reagents to α,β-unsaturated carbonyl compounds (see FIG. 2).

A few methods are reported for synthesizing racemic β-amino alcohols (Ref. 6). Additionally, enantiomerically pure β-amino alcohols are presently available through reactions of amino acids (7a), kinetic resolution of racemic mixes of amino alcohols (3a), or chromatographic methods (7b). The reduction of amino acids to the corresponding amino alcohols is currently economically feasible only for the naturally occurring L-amino acids. Kinetic resolution or chromatography result in the immediate loss of at least 50% of possible product and often involves laborious separations. The only synthetic methodology available for the direct synthesis of amino alcohols in high yields might be the amination of chiral epoxides. However, this method suffers from the limitations that chiral epoxides are not readily available, are expensive, and only mono-substituted and trans symmetrical disubstituted epoxides can be used or a mixture of products results as shown below in Equations (1) and (2).

where R' and R" are alkyl or aryl.

The high reactivity of the enamine double bond, the most reactive double bond known in the hydroboration reaction, potentially makes it possible for compounds to undergo hydroboration by chiral boranes, e.g. either mono- or diisopinocampheyl-borane, resulting in amino alcohols of high enantiomeric purity. A commercial need, therefore, exists for a safe, simple, straightforward economic process to produce chiral β-amino alcohols in high enantiomeric purity (or enantiomeric excess-ee). The present invention achieves this goal by utilizing bulky chiral organoboranes.

SUMMARY OF THE INVENTION

The present invention relates to a process for the synthesis of chiral beta-aminoalcohols of the structure:

wherein
$R^1$ and $R^2$ are each independently selected from hydrogen;
alkyl having from 1 to 20 carbons;
aryl having from 6 to 20 carbons;
or $R^1$ and $R^2$ together form a cyclic ring having from 4 to 10 carbons with the proviso that one of $R^1$ or $R^2$ contains a carbon atom;
$R^3$ and $R^4$ are each independently selected from alkyl or aryl groups;
$R^3$ and $R^4$ together form a ring structure including the nitrogen atom in the ring having from 4 to 10 carbons; or
$R^3$ and $R^4$ together form a ring structure including the nitrogen atom in the ring structure having from 4 to 10 carbon atoms and also includes a second heteroatom independently selected from oxygen, nitrogen or sulfur;
$R^5$ is independently selected from hydrogen, alkyl or aryl as defined hereinabove from a chiral or achiral enamine, which process comprises:
(a) contacting a chiral or achiral enamine of the structure wherein $R^1$, $R^2$, $R^3$, $R^4$, and $R^5$ are defined hereinabove with a chiral borane of the structure:

wherein $R^6$ is independently selected from an aliphatic group, aromatic group, arylalkyl group, or alicyclic group having 6 to 50 carbon atoms, each having at least one chiral atom, and
$R^7$ is independently selected from hydrogen or $R^6$,
in a dipolar aprotic solvent at a temperature of between about +50° and −50° C. at ambient pressure for a time effective to react with the C=C bond,
(b) contacting the reaction product of step (a) with solid or aqueous base and 5% to 50% by weight of a mild oxidizing agent is added gradually under ambient conditions for a time effective to produce the chiral beta-aminoalcohol wherein the chiral amino alcohol has an enantiomeric excess (ee) of one isomer over the other of about 50% or greater.

DETAILED DESCRIPTION OF THE INVENTION AND PREFERRED EMBODIMENTS

Definitions

As used herein:

"Dipolar aprotic liquid or solvent" refers to any of the conventional organic solvents having a dipole and no easily ionizable protons. Examples include, diethyl ether, dipropyl ether, dibutyl ether, pentane, hexane, decane, tetrahydrofuran, dioxane, methylene chloride, chloroform, carbon tetrachloride, FREON$^R$, benzene, toluene, dimethylformamide (DMF), dimethylacetamide (DMAC), diglyme, or combinations thereof. The ethers are preferred. "Chiral organic group" refers to any conventional organic compound having at least one chiral atom, some steric bulk having 6 to 100 carbon atoms (preferably between 6 and 50 carbon atoms) and capable of forming reactive organoborane. Conventional polynuclear aromatic alkaloids, terpenoids, steroids, etc. (see, for example, L. F. Fieser, *Topics in Organic Chemistry*, Reinhold Publishing Corp., New York, N.Y., 1963) are preferred. Terpene boranes are more preferred. The boron usually has two chiral groups.

"Mild oxidizing agent" refers, for example, to aqueous hydrogen peroxide and solid or aqueous sodium hydroxide, metachloroperbenzoic acid, sodium perborate, sodium percarbonate, monoperphthalic acid magnesium salt, trialkylamine N-oxides as a solid, or combinations thereof.

The β-monosubstituted and α,β-disubstituted enamines were used as substrates. The hydroboration was conducted with borane methyl sulfide (BMS), followed by methanolysis and oxidation with alkaline hydrogen peroxide (Equation 3 below) (8a, b).

(3)

$R^1$ = alkyl, aryl
$R^5$ = H, alkyl, aryl $NR^3R^4$ =

$R^1$, $R^2$, $R^3$, $R^4$ and $R^5$ are defined hereinabove and preferably as shown in the list.

It is possible to synthesize the corresponding β-amino alcohol in moderate to excellent yield (see Table 1 below) (8a,b). The formation of alkenes and other side products was reduced to less than 5% of the total yield by employing Me₃NO as the oxidant in place of NaOH(s)/H₂O₂ (9).

TABLE 1

SYNTHESIS OF β-AMINO ALCOHOLS FOR CORRESPONDING ENAMINES

| enamine[b] | amino alcohol[c] | yield, %[d] |
|---|---|---|
|  |  | 54 |
|  |  | 69 |
|  |  | 76 |
|  |  | 92 |
|  |  | 82 |

TABLE 1-continued
SYNTHESIS OF β-AMINO ALCOHOLS FOR CORRESPONDING ENAMINES

| enamine[b] | amino alcohol[c] | yield, %[d] |
|---|---|---|
| | | 70[e] |
| | | 52 |
| | | 86 |
| | | 64[e] |
| | | 66 |

Footnote to Table 1:
[a]Hydroboration carried out using BMS/THF at 25° C.
[b]Purity determined by 250 MHz $^1$H- and $^{13}$C-NMR.
[c]Purity determined by 250 MHz $^1$H- and $^{13}$C-NMR and capillary GC comparison to authentic samples.
[d]Isolated yield.
[e]Me$_3$NO used as the oxidant in place of H$_2$O$_2$.

The methodology was extended to include β,β-disubstituted enamines as shown below in Equation 4 (8c).

(4)

R$^1$ = alkyl, aryl
R$^2$ = H, alkyl, aryl
R$^5$ = hydrogen

1 R$^1$, R$^2$, R$^3$, R$^4$ and R$_5$ are defined hereinabove.

Borane methyl sulfide (BMS) and 9-borabicyclo[3.3.1-nonane] (9-BBN) were first examined as hydroboration reagents. The efficacy of three oxidants for the conversion of boronic esters to the corresponding amino alcohols (NaOH(s)/H$_2$O$_2$, sodium perborate, and trimethylamine-N-oxide) (8c) was examined.

Surprisingly, and in contrast to earlier experiments, it was found that, for β,β-disubstituted enamines, using NaOH(s)/H$_2$O$_2$ as the oxidant gave the highest yields of the corresponding β-amino alcohols and was the least cumbersome of the three oxidizing agents to work with (see Table 2) (8c).

TABLE 2
SYNTHESIS OF β-AMINO ALCOHOLS FROM CORRESPONDING ENAMINES

| enamine[a,b] | amino alcohol[c] | yield, %[d] |
|---|---|---|
| | | 64[e] |
| | | 84[f,g] |
| | | 62[e] |
| | | 95[e,f] |
| | | 91[f,g] |

[a]Purity verified by 250 MHz $^1$H- and $^{13}$C-NMR.
[b]All boronate esters were oxidized to the corresponding enamine using NaOH(s)/30% H$_2$O$^2$.
[c]Purity verified by 250 MHz $^1$H- and $^{13}$C-NMR and mass spectrum.
[d]Isolated yield.
[e]Hydroboration carried out using 1 equiv. BMS in THF at 25° C.
[f]Hydroboration carried out using 1 equiv. BMS in THF at 65° C.
[g]Hydroboration carried out using 1 equiv. 9-BBN in THF at 25° C. for 3 h.

TABLE 3
SYNTHESIS OF CHIRAL β-AMINO ALCOHOLS FROM CORRESPONDING ENAMINES

| enamine[a] | amino alcohol | yield, %[b] | ee, %[c] |
|---|---|---|---|
| | | 86[d] | 6 |

The early synthesis of chiral β-amino alcohols was performed using monoisopinocampheylborane as the hydroboration reagent (8b). The initial substrates were a series of 1-(dialkylamino)cycloalkenes. After hydroboration at −40° C., the resulting alkylboranes were methanolyzed, then oxidized with NaOH(s)/30% hydrogen peroxide to produce the corresponding chiral β-amino alcohols in high overall yields having low enantiomeric excesses (ee) ranging from 6% to 28% (see Table 3). This low ee is generally not high enough to be of general or commercial use.

TABLE 3-continued

SYNTHESIS OF CHIRAL β-AMINO ALCOHOLS FROM CORRESPONDING ENAMINES

| enamine[a] | amino alcohol | yield, %[b] | ee, %[c] |
|---|---|---|---|
| (N-piperidinyl cyclohexenyl enamine) | (2-piperidinyl cyclohexanol) | 66[d] | 26 |
| (N-morpholinyl cyclohexenyl enamine) | (2-morpholinyl cyclohexanol) | 86[e] | 14 |
| (N-morpholinyl cyclohexenyl enamine) | (2-morpholinyl cyclohexanol) | 84[f] | 21 |
| (N-morpholinyl cyclohexenyl enamine) | (2-morpholinyl cyclohexanol) | 59[e,g] | 28 |
| (N-methyl-N-benzyl cyclohexenyl enamine) | (2-(N-methyl-N-benzylamino) cyclohexanol) | 77[d] | 27 |

Footnote to Table 3
[a] All hydroborations carried out with monoisopinocampheyl-borane, followed by methanolysis and oxidation with NaOH/H$_2$O$_2$.
[b] Isolated yield.
[c] Determined by capillary GC analysis of the MCF derivative of the amino alcohol.
[d] Hydroboration carried out at −40° C.
[e] Hydroboration carried out at 0° C.
[f] Hydroboration carried out at −30° C.
[g] Diisopinocampheyl-borane used as a complexing agent to slow down the rate of hydroboration.

Surprisingly, this result represents the first known direct synthesis of chiral β-amino alcohols from achiral precursors. It is also possible using the present invention to start with an enamine having one or more chiral atoms and create additional chiral atoms in the product.

Low enantiomeric excesses were obtained using monoisopinocampheylborane. However, diisopinocampheylborane is a significantly more sterically demanding chiral organoborane. Although the overall product yields obtained with diisopinocampheylborane were lower than those for monoisopinocampheylborane, the enantiomeric excesses (ee) showed a dramatic improvement (see Table 4 below) (Ref. 10), being greater than 50% ee up to 99%, preferably about 60 to 99% ee.

TABLE 4

CONVERSION OF ENAMINES TO THE CORRESPONDING CHIRAL AMINO ALCOHOLS

| enamine | amino alcohol[a,c] | yield, % | ee, %[b] |
|---|---|---|---|
| (long chain pyrrolidinyl enamine) | (long chain β-amino alcohol with pyrrolidine) | 30[f] | — |
| (long chain morpholinyl enamine) | (long chain β-amino alcohol with morpholine) | 50[e] | 80 |
| (long chain morpholinyl enamine) | (long chain β-amino alcohol with morpholine) | 30[f] | 99 |

TABLE 4-continued
CONVERSION OF ENAMINES TO THE CORRESPONDING CHIRAL AMINO ALCOHOLS

| enamine | amino alcohol[a,c] | yield, % | ee, %[b] |
|---|---|---|---|
| (structure: H-C=C with morpholine N and ethyl) | (structure: HO-CH-CH with morpholine N and ethyl) | c,d | 60 |
| (structure: H-C=C with pyrrolidine N and phenyl) | (structure: HO-CH-CH with pyrrolidine N and phenyl) | c,d | 60 |
| (structure: H-C=C with morpholine N and phenyl) | (structure: HO-CH-CH with morpholine N and phenyl) | c,d | 60 |

[a] Absolute configuration not determined.
[b] Determined by chiral HPLC.
[c] Racemic alcohols synthesized for chiral HPLC analysis using 1) BMS, 25° C.; 2) MeOH; 3) H$_2$O$_2$/NaOH(s).
[d] Synthesized in low yields using 1) [d]Ipc$_2$BH, 25° C.; 2) H$_2$O$_2$/NaOH(s).
[e] Synthesized using 1) [d]Ipc$_2$BH, 0° C.; 2) H$_2$O$_2$/NaOH(s).
[f] Synthesized using 1) [d]Ipc$_2$BH, −25° C.; 2) H$_2$O$_2$/NaOH(s).
[g] Me$_3$NO used as the oxidant in place of H$_2$O$_2$/NaOH(s).

The highest asymmetric induction observed (greater than about 99% ee) results from hydroborations performed at −25° C. Hydroborations performed at about 0° C. produced about 80% ee. Even the reactions performed at 25° C. produced enantiomeric excesses of at least 60%, and the hydroborations were complete in about 30 minutes. Surprisingly for ketone enamines, trimethylamine-N-oxide is also the best oxidant for conversion of enamine-borane adducts to the corresponding chiral amino alcohols. On the other hand, for aldehyde enamines, NaOH(s)/30% hydrogen peroxide is the oxidant of choice. Further, because the product of the diisopinocampheylborane hydroboration is a trialkylborane, there are no boron-hydrogen bonds remaining in the enamine-borane adducts. Therefore, these adducts are oxidized directly without the intervening methanolysis which is usually required when using monoisopinocampheylborane. The synthesis appears to be general to all secondary amine groups.

This hydroboration of enamines is shown to be a versatile and convenient high-yield method for the synthesis of both racemic and enantiomerically pure β-amino alcohols. The generality of this reduction process coupled with the nearly total synthetic control of enamine structure is useful for the synthesis of virtually any racemic or enantiomerically pure β-amino alcohol The following Examples are presented for the purpose of explaining and describing the present invention. They are not to be construed as being limiting in any way.

General—All operations were carried out under a nitrogen atmosphere. All glassware, syringes, and needles were oven-dried at 110° C. and cooled to room temperature with nitrogen gas before use. Tetrahydrofuran (THF) was freshly distilled from sodium and benzophenone ketyl. Anhydrous ether was purchased and used directly. Enamines were synthesized according to literature procedures (8c) and purified by high-vacuum distillation before use. R-(+)-α-pinene was purified by stirring over lithium aluminum hydride (LiAlH$_4$) for 24 hr followed by distillation (12 Torr) from the LiAlH$_4$. $^1$H-NMR and $^{13}$C-NMR were obtained at 250 MHz. Chemical shifts are in δ units relative to internal tetramethylsilane (TMS). Enantiomeric excesses are determined by gas chromatography analysis of the menthyl chloroformate (MCF) derivatives of the amino alcohols or by high pressure liquid chromatography (HPLC) of the underivatized amino alcohols using a chiral stationary phase.

EXAMPLE 1

Synthesis of Diisopinocampheylborane (a) Aliquots (10 mmol) of diisopinocampheylborane (Ipc$_2$BH) were synthesized and stored under nitrogen at 0° C. for future use. To a 50-mL serum vial equipped with a magnetic stirring bar and sealed with a wired-on rubber septum was added by syringe R-(+)-e-pinene (23 mmol, 3.13 g. 4 mL). The vial was cooled to 0° C. under positive nitrogen gas pressure. Borane methyl sulfide (BMS) was added (10M, 1 mL, 10 mmol) dropwise with gentle stirring. The reaction mixture was allowed to stir at 0° C. for an additional 30 min. It was removed from the ice bath and stirred at 25° C. until all traces of solvent were gone and an intractable white solid formed. The Ipc$_2$BH synthesized can be stored under nitrogen at 0° C. for periods up to three months.

(b) Similarly, when Example 1(a) above is repeated except that R-(+)-α-pinene is replaced with a stoichiometrically equivalent amount of chiral bulky organic alkene, (R)-(+)-3-carene, R-(+)-2-carene, longifoglene or beta-pinene the corresponding chiral diorganic borane is produced in good yield.

EXAMPLE 2

Hydroboration of 1-(benzylmethylamino)cyclohexene with Monoisopinocampheylborane (IpcBH$_2$) at −40° C.

Lower Organic Bulk—High Product Yield—Low ee (a) The following procedure is representative. To a previously oven dried and nitrogen flushed 50-mL centrifuge tube equipped with a magnetic stirrer and sealed with a rubber septum was added 1-(benzylmethylamino)cyclohexene (8 mmol, 1,608 g) and 1 mL anhydrous diethyl ether. The solution was cooled to −40° C. and a 0.8 M solution of IpcBH$_2$ (10 mL, 8 mmol) in diethyl ether which had been previously cooled to −40° C. was slowly added. After 43 hr at −40° C., the reaction mixture was treated with methanol (1 mL, 25 mmol). The reaction mixture was stirred at −40° C. for 1 hr. The reaction mixture was transferred to a previously oven dried and nitrogen flushed 50-mL flask equipped with a magnetic stirrer. The reaction mixture was kept at 0° C. and solid NaOH (0.96 g, 24 mmol) was added. To this mixture, 30% hydrogen peroxide (about 8M, 2.4 mL, about 19.2 mmol) was slowly added. Caution—this is an exothermic reaction. The reaction mixture was stirred for an additional 1 hr at 25° C. The white solid that had formed was filtered off and washed with diethyl ether (3×25 mL). The ether was removed in vacuo from the filtrate, leaving a pale yellow oil. GC analysis demonstrated the oil to be a mixture of isopinocampheol and trans-2-(benzylmethylamino)cyclohexanol with a small amount of N-benzyl-N-methylcyclohexylamine. The oil was dissolved in 20 mL of methanol and then acidified with concentrated HCl. The acidified solution was stirred at 25° C. for an additional 15 min. The methanol was removed in vacuo, leaving a heavy, pale oil. The oil was washed with diethyl ether (3×25 mL). The ether was discarded and the oil layer contacted with fresh diethyl ether (25 mL). The reaction mixture was made basic with 6M NaOH (ag). The basic solution was extracted with diethyl ether (5×25 mL). The combined ether extracts were dried over anhydrous magnesium sulfate (MgSO$_4$). The MgSO$_4$ was filtered off and washed with diethyl ether (2×25 mL). The ether was removed in vacuo, leaving 1.79 g of pale yellow oil. GC analysis indicated that the oil still contained a large amount of isopinocampheol. The oil was acidified with concentrated HCl and 25 Ml of water was added. The acidic solution was stirred at 25° C. for an additional 15 min. and extracted with diethyl ether (4×25 mL). The reaction mixture was made basic with 6M NaOH (ag) and extracted with diethyl ether (4×25 mL). The combined ether extracts were dried over anhydrous MgSO$_4$. The MgSO$_4$ was filtered and washed with diethyl ether (2×25 mL). The ether was removed in vacuo, leaving crude trans-2-(benzylmethyl-amino)cyclohexanol (1.39 g, 77% yield). GC analysis showed that all of the isopinocampheol had been removed.

The menthyl chloroformate (MCF) derivative of the crude trans-2-(benzylmethylamino)cyclohexanol was prepared, using the literature method. Capillary GC analysis indicated a 27% ee.

EXAMPLE 3

Hydroboration of (E)-1 Morpholino-1-octene With Diisopinocampheylborane (Ipc$_2$BH)

(High Organic Bulk—Lower Product Yield—Higher ee)

The following procedure is representative. To an aliquot of Ipc$_2$BH (10 mmol) prepared as described in Example 1 above and cooled to 0° C., (E)-1-morpholine-1-octene (9.9 mmol, 2.13 g, 2.3 mL) was added, followed by anhydrous THF (10 mL). The resulting white suspension was stirred at 0° C. overnight until it became transparent, indicating that the hydroboration was complete. The reaction mixture was transferred by double-ended needle to a second 50-mL serum vial that had been previously equipped with a magnetic stirring bar, cooled under nitrogen, charged with NaOH(s) (560 mg, 14 mmol), and sealed with a wired-on rubber septum. 30% Hydrogen peroxide (H$_2$O$_2$) was added dropwise by syringe (CAUTION—H$_2$O$_2$ causes severe burns) resulting in an extremely vigorous exothermic reaction. The reaction mixture was stirred for an additional 30 min. at 0° C., followed by 30 min. additional stirring at 25° C. The organic layer was decanted from the sticky white solid that formed, the solid was washed with THF (3×10 mL), the THF fractions combined, and the THF removed in vacuo. The thick oil that remains was layered with methanol (15 mL) and acidified with concentrated HCl (12M, 1 mL. 12 mmol). The reaction was stirred for 30 min. at 25° C. The methyl boronic ester that formed was removed in vacuo along with the residual methanol, leaving a thick amber-colored oil. The oil was washed with diethyl ether (4×10 mL). The ether washes were discarded and the amino alcohol hydrochloride layered with fresh ether (25 mL) and cooled to 0° C. Solid sodium hydroxide, followed by 1–2 mL 3M NaOH(ag), was added to the reaction mixture with stirring until the aqueous layer was strongly basic to litmus paper. A thick white solid formed, and all color was in the ether layer. The ether was decanted into an Erlenmeyer flask, the white solid washed with ether (4×10 mL) and the combined ether fractions were dried over anhydrous MgSO$_4$. The MgSO$_4$ was filtered and washed with ether (2×10 mL). The ether was removed in vacuo, leaving crude (R)-1-morpholine-2-octanol (1.0 g, 47% yield, bp: 84°–85° C., at 0.16 Torr) as a transparent gold colored liquid.

Chiral HPLC analysis of the distilled (R)-1-morpholino- 2-octanol indicated 80% ee.

(b) Similarly when Example 2(a) above is repeated except that the enamine is replaced by a stoichiometrically equivalent amount of any of the enamines listed in Table 1, 2, 3 or 4 above or from Example 1(b) above, the corresponding chiral amino alcohol is obtained in good yield, having a high ee of greater than about 50%.

While only a few embodiments of the invention have been shown and described herein, it will become apparent to those skilled in the art that various modifications and changes can be made in the asymmetric synthesis of beta-amino alcohols from chiral and achiral enamines using bulky chiral organoboranes without departing from the spirit and scope of the present invention. All such modifications and changes coming within the scope of the appended claims are intended to be carried out thereby.

We claim:

1. A process for the synthesis of a chiral beta-aminoalcohol of the structure:

wherein
$R^1$ and $R^2$ are each independently selected from hydrogen, alkyl having from 1 to 20 carbons; aryl having from 6 to 20 carbons;
or $R^1$ and $R^2$ together form a cyclic ring having from 4 to 10 carbon atoms, with the proviso that one of $R^1$ or $R^2$ contains a carbon atom;
$R^3$ and $R^4$ are each independently selected from alkyl or aryl, or $R^3$ and $R^4$ together form a ring structure including the nitrogen atom in the ring having from 4 to 10 carbon atoms, or
$R^3$ and $R^4$ together form a ring structure having from 4 to 10 carbon atoms including the nitrogen atom in the ring structure and includes in the ring a second heteroatom independently selected from oxygen, nitrogen or sulfur;
$R^5$ is independently selected from hydrogen, alkyl or aryl as defined hereinabove;
from a chiral or achiral enamine, which process comprises:
(a) reacting a chiral or achiral enamine of the structure wherein $R^1$, $R^2$, $R^3$, $R^4$ and $R^5$ are defined hereinabove with a chiral borane of the structure:

wherein $R^6$ is independently selected from an aliphatic group, aromatic group, arylalkyl group, or alicyclic group having 6 to 50 carbon atoms, each group including at least one chiral atom, and
$R^7$ is independently selected from hydrogen or $R^6$,
in a dipolar aprotic solvent at a temperature of between about 50° C. and −50° C. at ambient pressure for a time effective to react with the C=C bond,
(b) reacting the reaction product of step (a) with solid or aqueous base and 5% to 50% by weight of a mild oxidizing agent is added gradually under ambient conditions for a time effective to produce the chiral beta-amino alcohol, wherein the amino alcohol product has an enantiomeric excess of one enantiomer over the other of about 50% or greater than 50%.

2. The process of claim 1 wherein the enamine is achiral.

3. The process of claim 2 wherein the enantomeric excess (ee) of one isomer over the other is between about about 60% and 99%.

4. The process of claim 1 wherein the mild oxidizing agent is selected from hydrogen peroxide with solid or aqueous sodium hydroxide or trimethylamine N-oxide as a solid.

5. The process of claim 1 wherein
$R^1$ is hydrogen,
$R^2$ is independently selected from alkyl having 1 to 10 carbon atoms, or aryl having 6 to 10 carbon atoms,
$R^3$ and $R^4$ form a ring structure including a nitrogen atom having 4 to 8 carbon atoms optionally also including a second nitrogen atom or an oxygen atom in the ring.

6. The process of claim 1 wherein the enamine is independently selected from any of the following structures:

7. The process of claim 6 wherein the chiral borane is diisopinocampheylborane.

8. The process of claim 1 wherein the dipolar aprotic solvent is independently selected from diethyl ether, dipropyl ether, dibutyl ether, tetrahydrofuran, dioxane, pentane, hexane, decane, methylene chloride, chloroform, carbon tetrachloride, FREON ®, benzene, toluene, dimethylformamide, dimethylacetamide, diglyme , or mixtures thereof.

9. The process of claim 8 wherein the mild oxidizing agent is selected from hydrogen peroxide in the presence of solid or aqueous base, metachloro-perbenzoic acid, sodium perborate, sodium percarbonate, monoperphthalic acid, magnesium salt or trimethylamine N-oxide, or combinations thereof.

10. The process of claim 9 wherein the chiral organoborane is independently selected from diisopinocampheylborane, di-4-isocaranylborane, diisoaponinyl-campheylborane, 2,5-dimethylboralanes, di-2-isocaranylborane, dilongifolylborane, or combinations thereof.

11. The process of claim 10 wherein the enamine is independently selected from any of the following structures:

12. The process of claim 11 wherein the dipolar aprotic solvent is selected from diethyl ether, dipropyl ether, dibutyl ether, tetrahydrofuran, dioane, diglyme or mixtures thereof.

13. The process of claim 12 wherein the mild oxidizing agent is independently selected from hydrogen peroxide in the presence of aqueous or solid sodium hydroxide or trimethylamine-N-oxide (solid).

14. The process of claim 13 wherein the borane is chiral diisopinocampheyl-borane.

15. A process for the synthesis of a chiral beta-amino alcohol having an enantiomeric excess of 50% or greater of one enantiomer over the other of the structure:

wherein
- $R^1$ and $R^2$ are each independently selected from hydrogen, alkyl having from 1 to 20 carbons; aryl having from 6 to 20 carbons; or
- $R^1$ and $R^2$ together form a cyclic ring having from 4 to 10 carbon atoms, with the proviso that one of $R^1$ or $R^2$ contains a carbon atom;
- $R^3$ and $R^4$ are each independently selected from alkyl as defined herein above;
- $R^3$ and $R^4$ together form a ring structure including the nitrogen atom in the ring having from 4 to 10 carbon atoms; or
- $R^3$ and $R^4$ together form a ring structure having from 4 to 10 carbon atoms said ring structure including the nitrogen atom and further includes in the ring a second heteroatom independently selected from oxygen, nitrogen or sulfur;
- $R^5$ is independently selected from hydrogen, alkyl or aryl as defined hereinabove;

from an enamine, which process comprises:
(a) reacting an enamine of the structure wherein $R^1$, $R^2$, $R^3$, $R^4$, and $R^5$ are defined hereinabove with a chiral borane of the structure:

wherein $R^6$ and $R^7$ are each independently selected from an aliphatic group, aromatic group, arylalkyl group, or alicyclic group having 6 to 50 carbon atoms wherein, each of $R^6$ and $R^7$ contains at least one chiral carbon atom, and in a dipolar solvent at a temperature of between about +50° and −50° C. at ambient pressure for a time effective to react with the C=C bond,

(b) reacting the product of step (a) with solid or aqueous base and 5 to 50% by weight of a mild oxidizing agent is added gradually under ambient conditions for a time effective to produce the chiral beta-amino alcohol, wherein the amino alcohol product has an enantiomeric excess of one enantiomer over the other enantiomer of about 50% or greater than 50%.

16. A process for the synthesis of a chiral beta-amino alcohol having an enantiomeric excess of 50% or greater of one enantiomer over the other of the structure:

wherein
- $R^1$ and $R^2$ are each independently selected from hydrogen, alkyl having from 1 to 20 carbons; aryl having from 6 to 20 carbons; or
- $R^1$ and $R^2$ together form a cyclic ring having from 4 to 10 carbon atoms, with the proviso that one of $R^1$ or $R^2$ contains a carbon atom;
- $R^3$ and $R^4$ are each independently selected from alkyl as defined herein above;
- $R^3$ and $R^4$ together form a ring structure including the nitrogen atom in the ring having from 4 to 10 carbon atoms; or
- $R^3$ and $R^4$ together form a ring structure having from 4 to 10 carbon atoms said ring structure including the nitrogen atom and further includes in the ring a second heteroatom independently selected from oxygen, nitrogen or sulfur;
- $R^5$ is independently selected from hydrogen, alkyl or aryl as defined hereinabove;

from an enamine, which process comprises:
(a) reacting an enamine of the structure wherein $R^1$, $R^2$, $R^3$, $R^4$, and $R^5$ are defined hereinabove, with a chiral organoborane independently selected from diisopinocampheylborane, di-4-isocaranylborane, diisoponinylcampheylborane, 2,5-dimethylboralane, di-2-isocaranylborane, dilongifolylborane, or combinations thereof, and a dipolar aprotic solvent at a temperature of between about +50° and −50° C. at ambient pressure for a time effective to react with the C=C bond, (b) reacting an the product step (a) with solid or aqueous base and 5 to 50% by weight of a mile oxidizing agent is added gradually under ambient conditions for a time effective to produce the chiral beta-amino alcohol, wherein the amino alcohol product has an enantiomeric excess of one enantiomer over the other enantiomer of about 50% or greater than 50%.

17. The process of claim 1 wherein the chiral borane is diisopinocampheylborane.

* * * * *